(12) United States Patent
Amrein et al.

(10) Patent No.: US 7,022,122 B2
(45) Date of Patent: *Apr. 4, 2006

(54) DEVICE FOR CONNECTING A LONGITUDINAL BAR TO A PEDICLE SCREW

(75) Inventors: Thomas Amrein, Horw (CH); Martin Hess, Hölstein (CH)

(73) Assignee: Synthes (U.S.A.), West Chester, PA (US)

( * ) Notice: Subject to any disclaimer, the term of this patent is extended or adjusted under 35 U.S.C. 154(b) by 259 days.

This patent is subject to a terminal disclaimer.

(21) Appl. No.: 10/122,405

(22) Filed: Apr. 16, 2002

(65) Prior Publication Data

US 2003/0023240 A1    Jan. 30, 2003

Related U.S. Application Data

(63) Continuation of application No. 09/341,963, filed as application No. PCT/CH97/00019 on Jan. 22, 1997, now Pat. No. 6,371,957.

(51) Int. Cl.
*A61B 17/70* (2006.01)

(52) U.S. Cl. ...................................................... 606/61
(58) Field of Classification Search ............. 606/60, 606/61, 72, 73
See application file for complete search history.

(56) References Cited

U.S. PATENT DOCUMENTS

| | | | |
|---|---|---|---|
| 4,946,458 A | 8/1990 | Harms et al. | |
| 5,207,678 A | 5/1993 | Harms et al. | |
| 5,261,909 A | 11/1993 | Sutterlin et al. | |
| 5,352,226 A | 10/1994 | Lin | |
| 5,429,639 A | 7/1995 | Judet | |
| 5,443,467 A | 8/1995 | Biedermann et al. | |
| 5,466,237 A | 11/1995 | Byrd, III et al. | |
| 5,474,551 A | 12/1995 | Finn et al. | |
| 5,474,555 A | 12/1995 | Puno et al. | |
| 5,499,983 A | 3/1996 | Hughes | |
| 5,501,684 A | 3/1996 | Schlapfer et al. | |
| 5,520,690 A | 5/1996 | Errico et al. | |
| 5,527,314 A | 6/1996 | Brumfield et al. | |
| 5,531,746 A | 7/1996 | Errico et al. | |
| 5,534,001 A | 7/1996 | Schlapfer et al. | |
| 5,549,608 A | 8/1996 | Errico et al. | |
| 5,554,157 A | 9/1996 | Errico et al. | |
| 5,575,791 A | 11/1996 | Lin | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,607,426 A | 3/1997 | Ralph et al. | |

(Continued)

FOREIGN PATENT DOCUMENTS

DE    195 09 332 C1    8/1996

(Continued)

*Primary Examiner*—David O. Reip
(74) *Attorney, Agent, or Firm*—Jones Day

(57) ABSTRACT

The invention is directed to a device for connecting a longitudinal bar to a pedicle screw for fixation of the spine. The device includes a body having an axis, an upper end, a lower end, a hole coaxial with the axis, and a through hole positioned perpendicular to the axis. The device also includes a coller chuck slidably disposed within the hole. The coller chuck includes a through hole substantially aligned with the through hole of the body for receiving the longitudinal bar, and a chamber defined by elastic tongues for receiving the head of the pedicle screw.

21 Claims, 8 Drawing Sheets

U.S. PATENT DOCUMENTS

| | | |
|---|---|---|
| 5,609,593 A | 3/1997 | Errico et al. |
| 5,609,594 A | 3/1997 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,683,392 A | 11/1997 | Richelsoph et al. |
| 5,688,273 A | 11/1997 | Errico et al. |
| 5,690,630 A | 11/1997 | Errico et al. |
| 5,728,098 A | 3/1998 | Sherman et al. |
| 5,733,285 A | 3/1998 | Errico et al. |
| 5,735,853 A | 4/1998 | Olerud |
| 5,741,255 A | 4/1998 | Krag et al. |
| 5,782,831 A | 7/1998 | Sherman et al. |
| 5,782,833 A | 7/1998 | Haider |
| 5,797,911 A | 8/1998 | Sherman et al. |
| 5,810,819 A | 9/1998 | Errico et al. |
| 5,817,094 A | 10/1998 | Errico et al. |
| 5,863,293 A | 1/1999 | Richelsoph |
| 5,879,350 A | 3/1999 | Sherman et al. |
| 6,063,090 A | 5/2000 | Schläpfer |
| 6,132,432 A | 10/2000 | Richelsoph |

FOREIGN PATENT DOCUMENTS

| | | |
|---|---|---|
| EP | 0 242 708 | 10/1987 |
| EP | 0 330 881 A1 | 9/1989 |
| WO | WO 94/00066 | 1/1994 |
| WO | WO 98/34554 | 8/1998 |

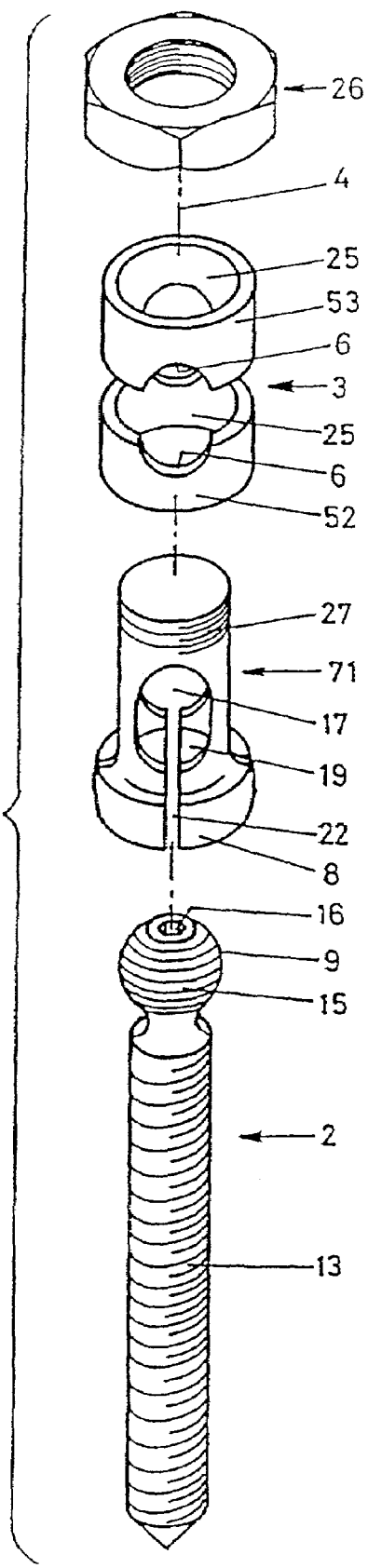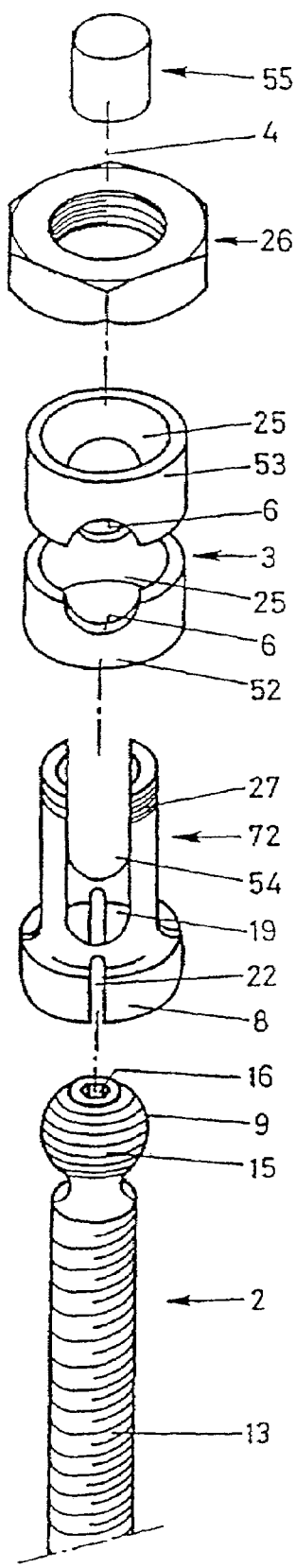

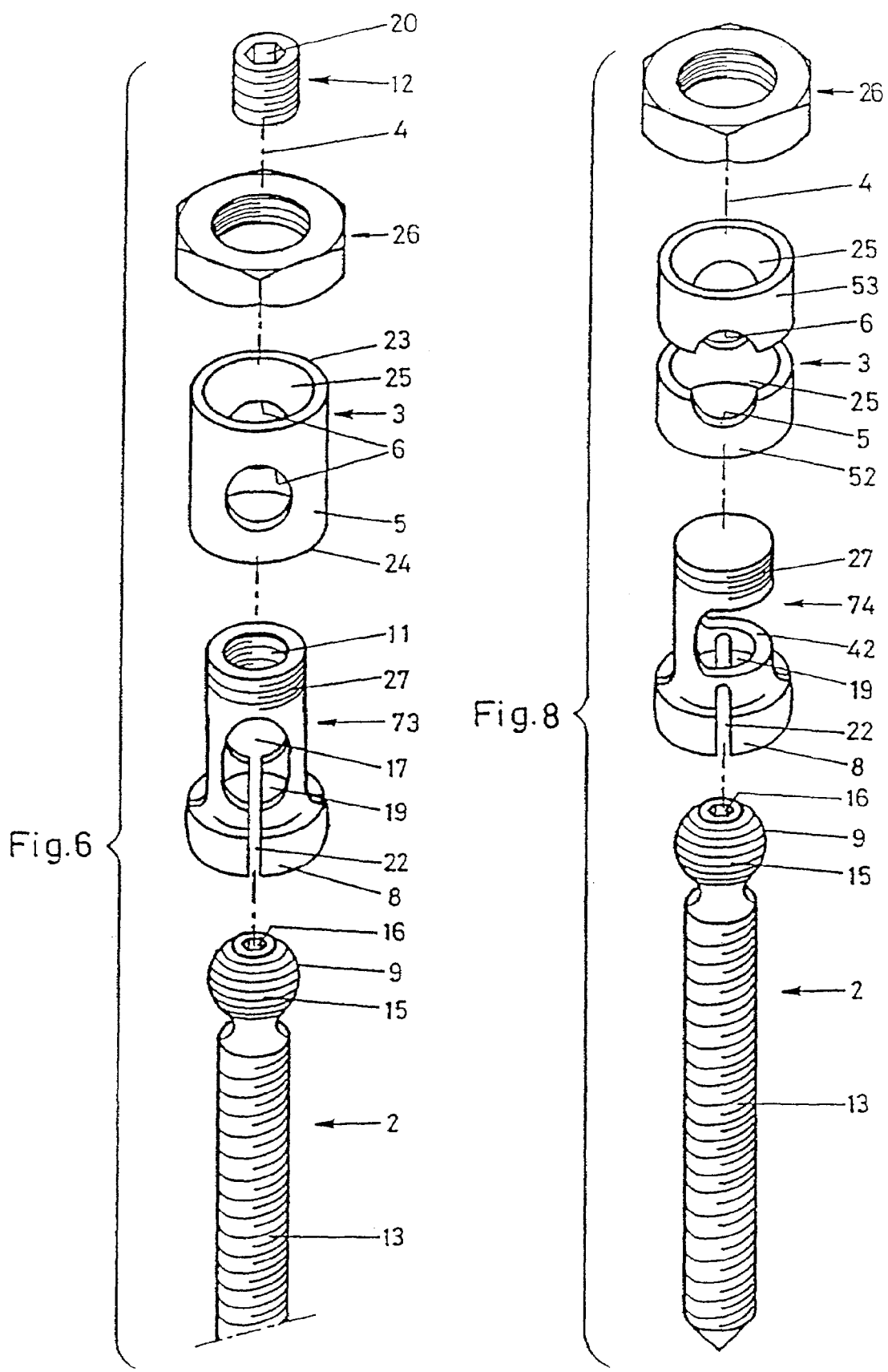

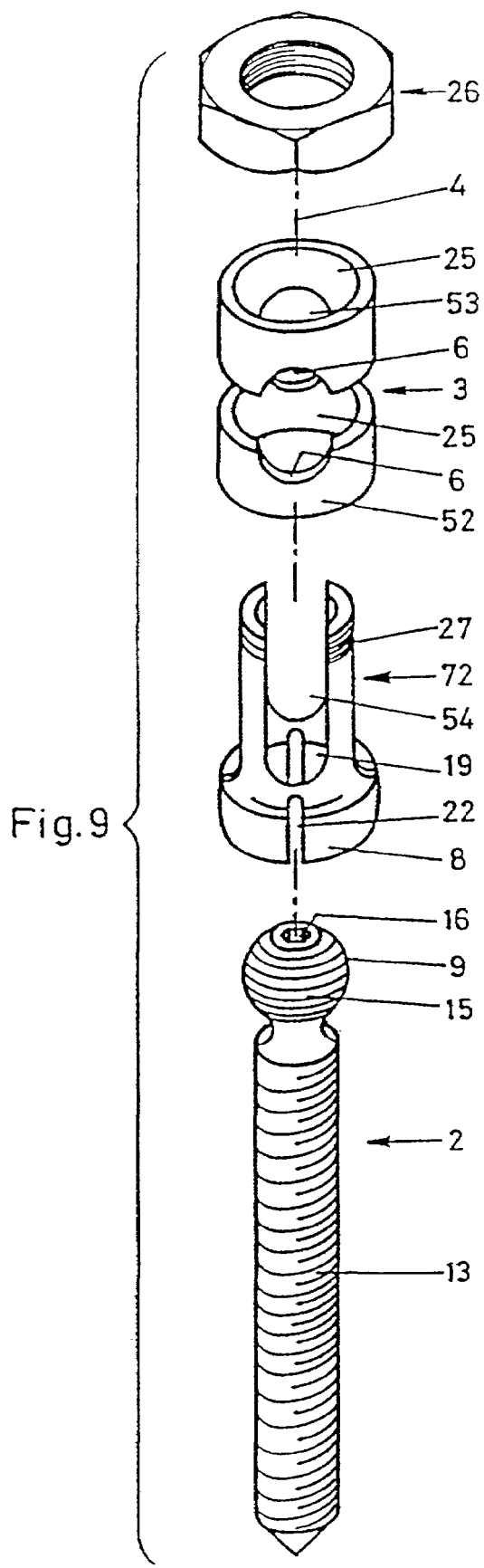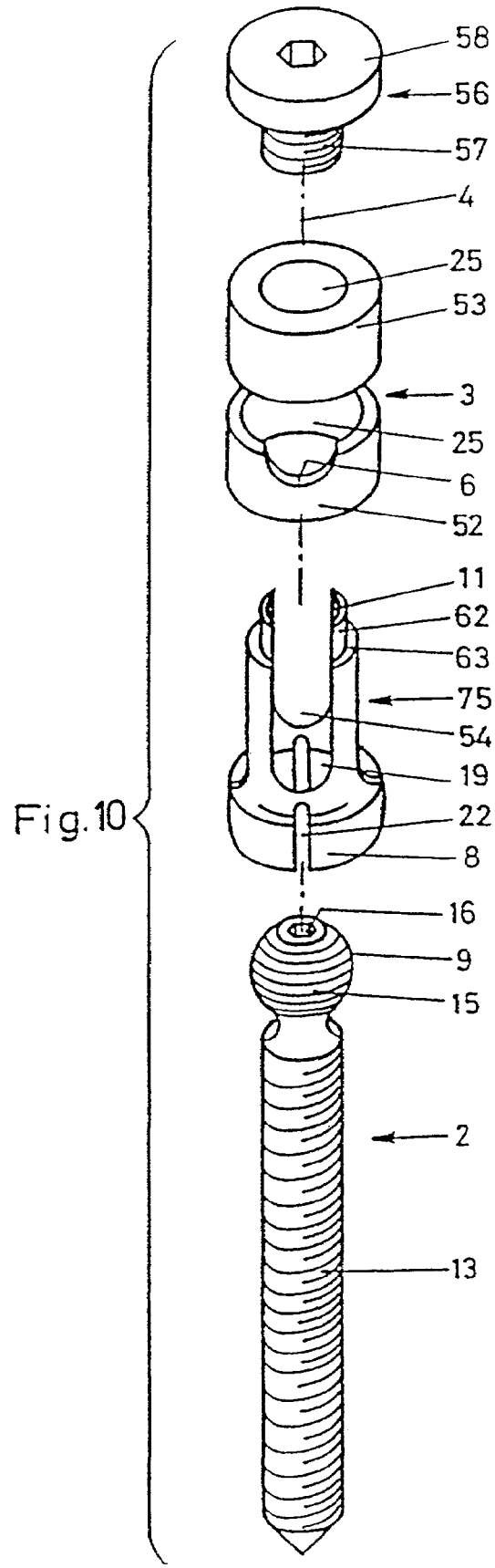

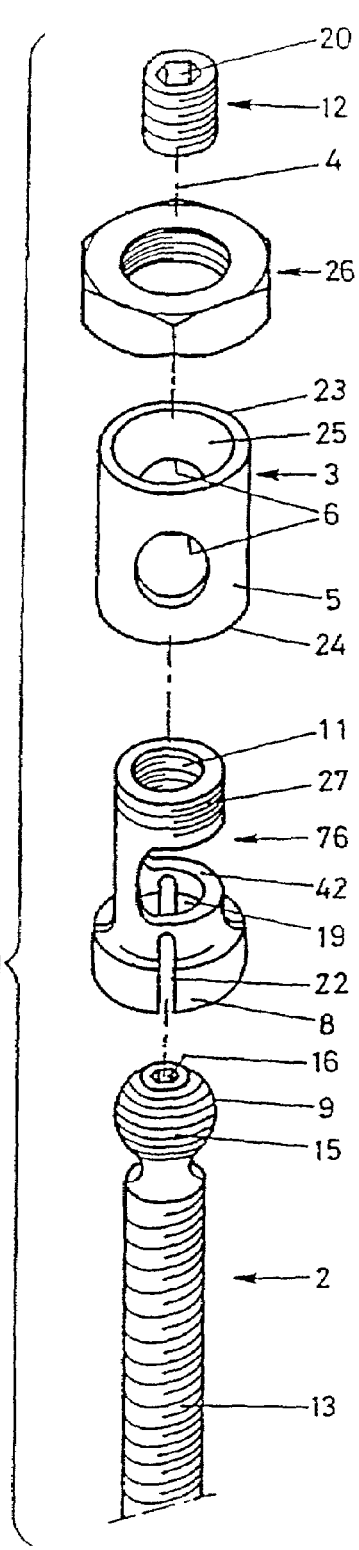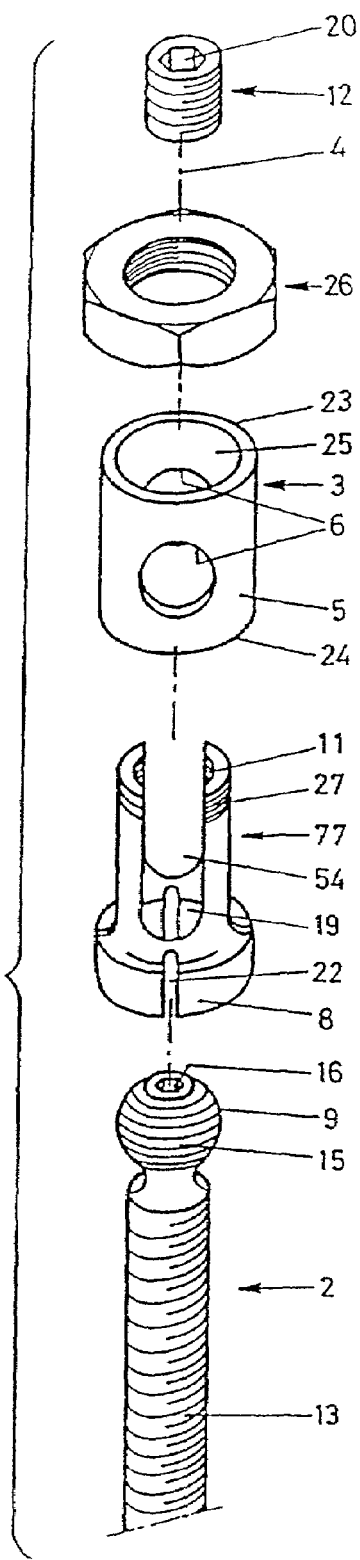

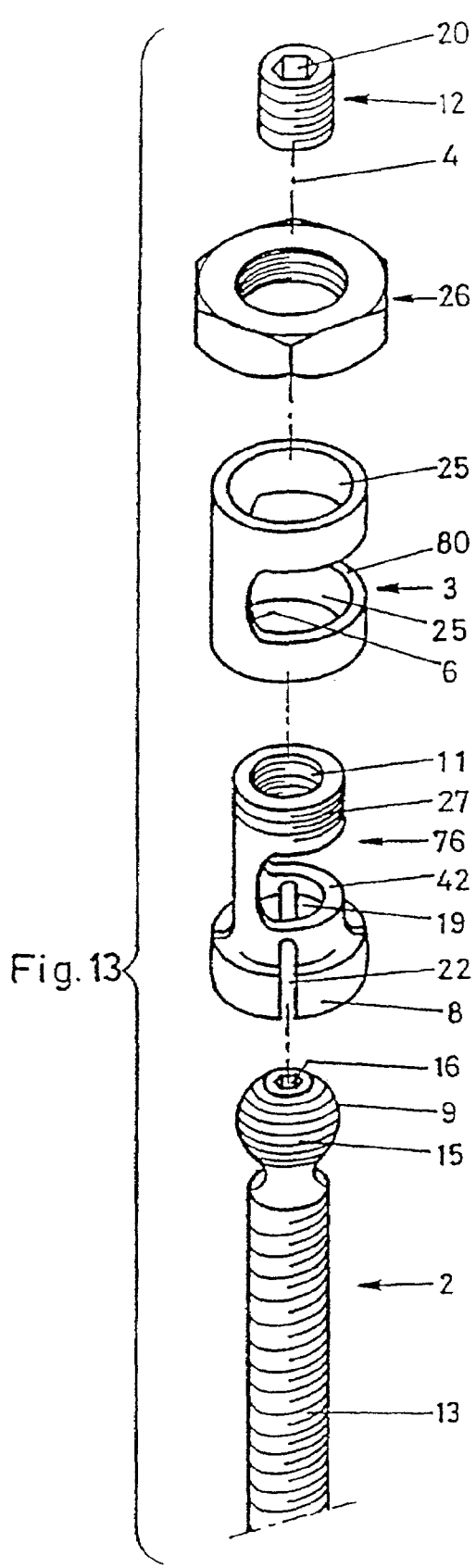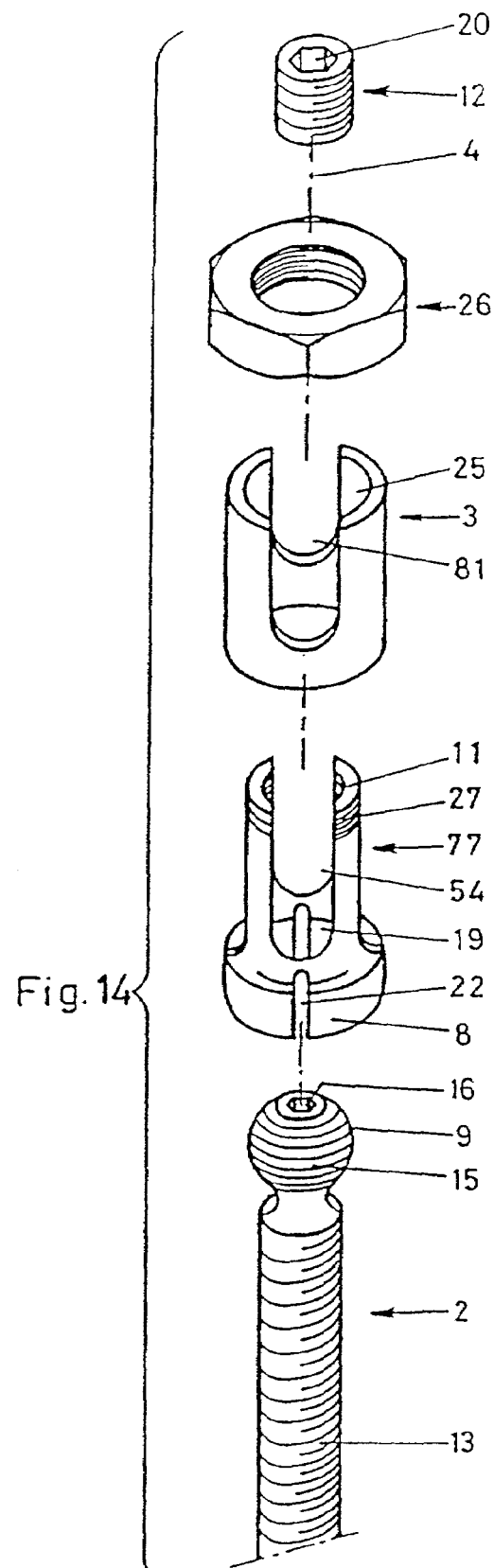

DEVICE FOR CONNECTING A LONGITUDINAL BAR TO A PEDICLE SCREW

CROSS REFERENCE TO RELATED APPLICATIONS

This is a continuation of U.S. patent application Ser. No. 09/341,963, now U.S. Pat. No. 6,371,957, filed Jul. 21, 1999, which is a continuation of PCT International Application No. PCT/CH97/00019, filed Jan. 22, 1997.

FIELD OF THE INVENTION

This invention concerns a device for connecting a longitudinal bar to a pedicle screw.

BACKGROUND OF THE INVENTION

From the related art, a large number of pedicle screws for fixation of the spinal column are already known; these known pedicle screws have the advantage that the individual pedicle screw can be attached to or removed from the longitudinal bar at any time without having to dismantle the entire fixation system. Such a pedicle screw is known from European Patent No. 330, 881 B, for example.

The disadvantage of this and similar pedicle screws is the relatively complicated locking mechanisms for securing the longitudinal bar inserted into the open pedicle screw head. Furthermore, in most cases the head of the screw can be aligned with the position of the longitudinal bar only to a limited extent, necessitating complicated bending of the longitudinal bar to correct the angle.

SUMMARY OF THE INVENTION

This invention will provide a remedy in this regard. This invention is based on the problem of creating a device for connecting a longitudinal bar to a pedicle screw, said device being easy to handle and permitting bending of the pedicle screw within a certain range.

The present invention relates to a spinal fixation system including a longitudinal member positionable along the spinal column, a fastener for engaging a vertebra, and a connector for connecting the fastener and the longitudinal member. One part of the connector is a body having a through hole for receiving the longitudinal member and an opening in the bottom surface leading to the interior of the body. Another part of the connector is a collet chuck configured and dimensioned to be slidably received in the interior of the body. The collet chuck has a through hole alignable with the body's through hole for insertion of the longitudinal member in the connector, a plurality of resilient tongues, and a chamber defined by inner surfaces of the tongues and configured and dimensioned to receive the fastener head. The tongues flex outward for receiving the fastener head in the chamber and flex back inward for retaining the fastener head in the chamber. The connector also includes a locking element for securing the longitudinal member in the body and collet chuck through holes. Engagement of the locking element results in inward movement of the tongue and thereby secures the fastener at a surgeon selected angle.

In one embodiment, the desired number of devices according to this invention can be aligned on a longitudinal bar and can be simply snapped onto the pedicle screw with a spherical head already implanted in the vertebrae, so that a primary connection between the longitudinal bar and the pedicle screw is established. Other embodiments of the device according to this invention permit subsequent insertion of the longitudinal bar from the side or from above. By screwing the set screw into the fixation device, the longitudinal bar is locked axially and rotationally in the device at the same time, and the device is secured in a stable angular position. The set screw presses on the longitudinal bar inserted into the device, and the longitudinal bar presses on the bushing of the fixation device, and the bushing braces the collet chuck on the preferably spherical head of the pedicle screw by way of corresponding, preferably conical inside surfaces of the bushing and outside surfaces of the collet chuck.

Other embodiments in turn permit sequential and independent locking of the longitudinal bar and rotation of the device with respect to the pedicle screw.

Thus, in comparison with known devices, the device according to this invention offers the advantage that the pedicle screws can not only be secured exactly perpendicular to the longitudinal bar but also permit an angle bend of up to ±25°. This is especially important if the longitudinal bar has not been bent accurately, which leads to major problems in assembly with traditional systems.

A preferred refinement of the device according to this invention consists of the fact that it also includes a pedicle screw with a preferably spherical head. The head of the pedicle screw is preferably provided with structuring in the form of transverse grooves or transverse ribs to achieve better fixation (bracing against the collet chuck). To be able to screw these pedicle screws into the bone, they are preferably provided with a hexagon socket in the spherical head.

BRIEF DESCRIPTION OF THE DRAWINGS

The figures show:

FIG. 4: a perspective view of one variant of the device shown in FIG. 1 with an adjusting nut and a divided bushing;

FIG. 5: a perspective view of one variant of the device shown in FIG. 4 with a channel on the collet chuck that is open at the top and with a securing pin;

FIG. 6: a perspective view of one variant of the device shown in FIG. 1 with an adjusting nut for securing the spherical head of the pedicle screw and a set screw for locking the longitudinal bar;

FIG. 8: a perspective view of one variant of the device shown in FIG. 5 with a collet chuck that is open at the side to accommodate the longitudinal bar and an adjusting nut as a chucking means for locking the longitudinal bar while at the same time securing the spherical head of the pedicle screw;

FIG. 9: a perspective view of the device shown in FIG. 5 without a securing pin;

FIG. 10: a perspective view of one variant of the device shown in FIG. 5 with a set screw and an inside thread in the collet chuck;

FIG. 11: a perspective view of one variant of the device shown in FIG. 8 with an adjusting nut for securing the spherical head of the pedicle screw and with a set screw for locking the longitudinal bar;

FIG. 12: a perspective view of one variant of the device shown in FIG. 11 with a collet chuck that is open at the top;

FIG. 13: a perspective view of one variant of the device shown in FIG. 11 with a through hole which is open at the side in the bushing; and FIG. 14: a perspective view of one variant of the device shown in FIG. 12 with a through hole which is open at the top in the bushing.

DETAILED DESCRIPTION OF THE INVENTION

Figure 1:
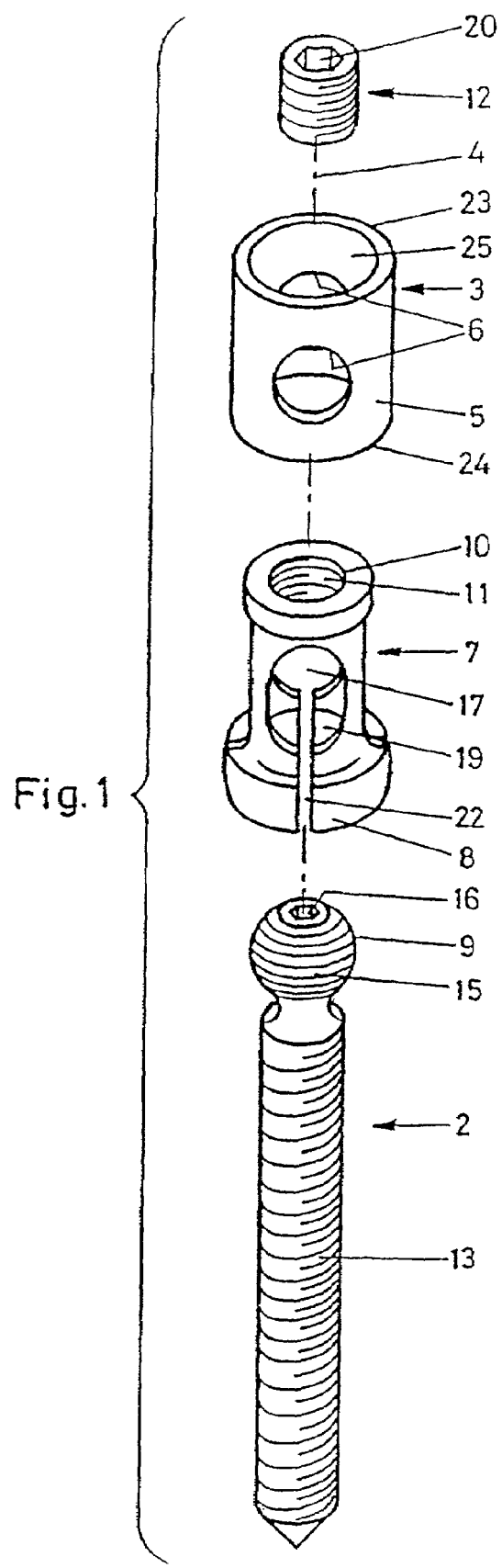
FIG. 1: an exploded perspective view of the device according to this invention with a longitudinal bar, a pedicle screw with a spherical head and a set screw.
Figure 2:
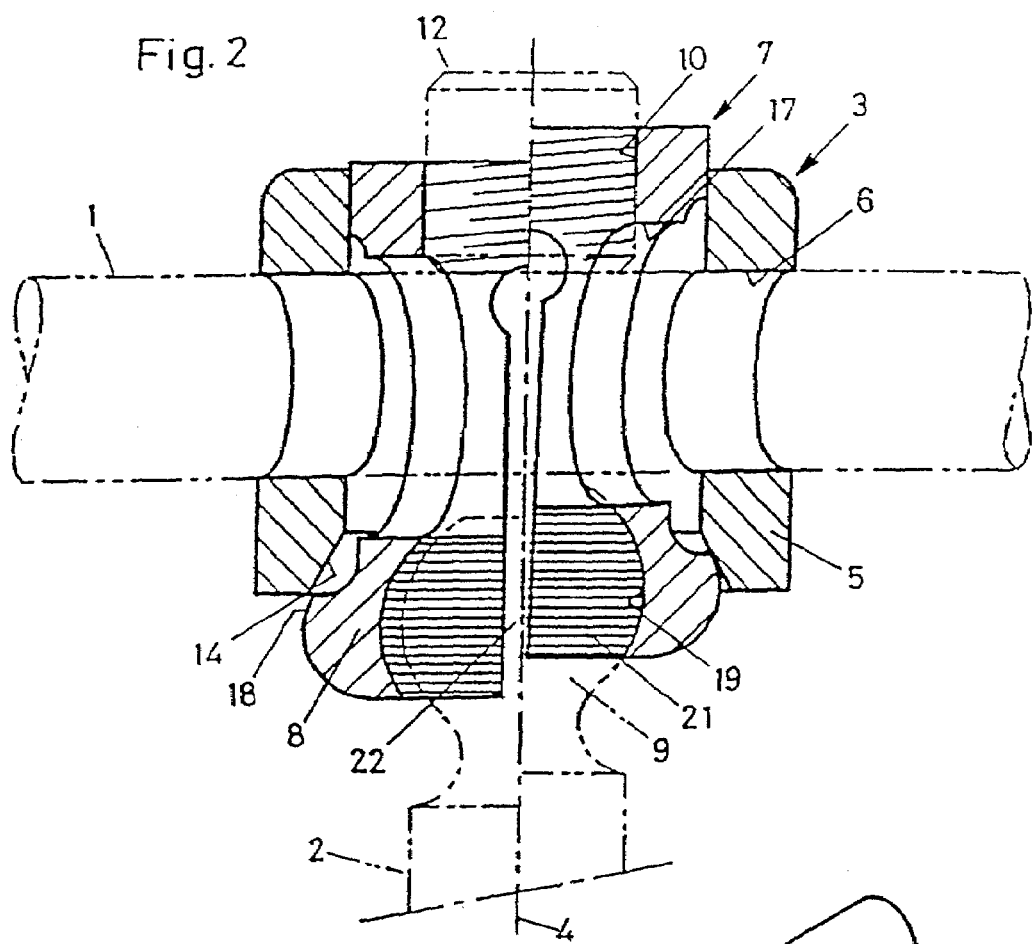
FIG. 2: a slotted longitudinal section through the device according to this invention as shown in the plane of the drawing in FIG. 1.

The device according to this invention illustrated in FIGS. 1 and 2 consists essentially of a body 3 in the form of a hollow cylindrical bushing with an axis 4 (axis of the hollow cylinder) and a hollow cylindrical collet chuck 7 arranged coaxially so it can slide in the interior of the body 3.

The body 3 has a through hole 6 running across the axis 4—intersecting the cylindrical surface of the hollow cylinder at two points symmetrically with the axis 4—and the collet chuck 7 has a through hole 17 running across the axis 4. Insertion of a longitudinal bar 1 running across the axis 4 is made possibly by the aligned arrangement of the through holes 6 and 17 as illustrated in FIG. 2.

In its upper part, the collet chuck 7 is secured within the (hollow cylindrical) body 3 by a press fit and can be displaced axially with respect to the body 3 when the relatively high force of the press fit is overcome.

The (hollow cylindrical) body 3 and the collet chuck 7 are preferably in a rotationally locked arrangement relative to one another, e.g., by means of suitable groove/channel guides running axially. The collet chuck 7 is designed with tongues 8 spring mounted against the cylinder axis 4 and pointing downward; the spherical head 9 of a pedicle screw 2 can be snapped from below with a spring action into the chamber formed by these tongues.

Figure 3:
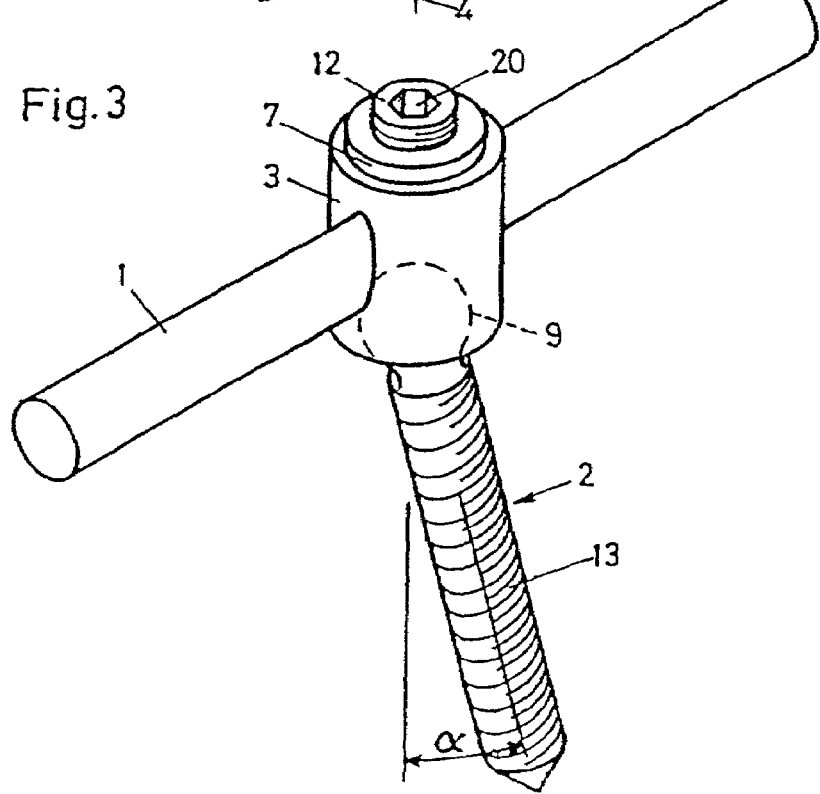
FIG. 3: a perspective view of the device according to FIG. 1 in the mounted state after locking the longitudinal bar and the pedicle screw by means of the set screw.

A hole 10 with an inside thread 11 is provided in the upper part of the collet chuck 7 to accommodate a set screw 12 with a hexagonal socket head 20 which can exert a force on a longitudinal bar 1 inserted into the device, so the longitudinal bar 1 is locked axially and rotationally with respect to the body 3, as indicated in FIG. 3. The collet chuck 7 is designed at its lower end such that the screw shaft 13 of the pedicle screw 2 connected to the spherical head 9 can be locked at an angle α of −25° to +25° with respect to the axis 4.

At its lower end 24, the body 3 has a conical inside surface 14 which becomes wider toward the lower end and can come into sliding contact with a suitably designed conical outside surface 18 of the free ends of the tongues 8 of the collet chuck 7. As soon as the set screw 12 abuts against the longitudinal bar 1 inserted into the device, the collet chuck 7 begins to push upward against the body 3. This process is illustrated in FIG. 2, where the left half of the figure shows the condition before pushing collet chuck 7 upward, and the right half shows the conical surfaces 14 and 18 slipping past one another as the collet chuck 7 is pushed upward, with the tongues 8 of the collet chuck 7, which are designed with a spring action due to the slot 22 being pushed toward cylinder axis 4, so that the hollow spherical cavity 19 is reduced in size, and the head 9 of the pedicle screw 2 inserted into it is gripped securely. To optimize the locking of the head 9, it is provided with a structuring 15, preferably in the form of transverse grooves or transverse ribs. Otherwise, pedicle screw 2 corresponds to the known screw designs and is expediently provided with a hexagonal socket head 16.

The hollow spherical cavity 19 may in turn be provided with a structuring 21, preferably in the form of transverse grooves or transverse ribs. A combination of structuring 21 and structuring 15 is possible to further improve the fixation effect of the head 9 in the hollow spherical cavity 19.

The hollow spherical cavity 19 is preferably designed with a shape complementary to that of the head 9 of the pedicle screw 2 to be accommodated in it.

The variant shown in FIG. 4 of the device according to this invention illustrates the use of a body 3, which is divided into a bottom part 52 and a top part 53 across the axis 4 in the middle of the through hole 6, in combination with an adjusting nut 26. The bottom part 52 of the body 3 must be so tall that the longitudinal bar 1 is always in contact with the bottom part 52.

The collet chuck 71 differs from the collet chuck 7 shown in FIG. 1 only in that the inside thread 11 on the upper end has been replaced by an outside thread 27 for use of an adjusting nut 26. When tightened, the adjusting nut 26 presses on the top part 53 of body 3, which subsequently presses directly on longitudinal bar 1. The longitudinal bar 1 is subsequently pressed against the bottom part 52 of the body 3, and then it locks the spherical head 9, as shown in FIG. 2.

The variant shown in FIG. 5 of the device according to this invention differs from the variant illustrated in FIG. 9 only in that one peg 55 prevents the collet chuck 72, which has been weakened by the channel 54, from collapsing when the adjusting nut 26 is tightened. To prevent this peg 55 from falling out, it is advantageously provided with an outside thread and screwed in.

The variant shown in FIG. 6 of the device according to this invention differs from the variant illustrated in FIG. 4 only in that
a) the collet chuck 73 has an inside thread 11 in addition to outside thread 27, and
b) the body 3, which is in one piece, and the through hole 6 are positioned with respect to the through hole 17 so that only the spherical head 9 is locked when the adjusting nut 26 is tightened. This permits distraction or compression with a stable angular position. The adjusting nut 26 presses on the body 3, and the resulting bracing of the body 3 with the collet chuck 73 ensures fixation of the spherical head 9 of the pedicle screw 2 without locking the longitudinal bar 1. The longitudinal bar 1 is pressed separately with the help of the set screw 12 against the lower edge of the through hole 6 of the body 3. Therefore, the body 3 is further wedged with the collet chuck 73, which leads to a greater clamping effect on the spherical head 9. The through hole 6 must be positioned in the body 3 so that the longitudinal bar 1 also rests on the lower edge of the through hole 6 after tightening the adjusting nut 26.

Figure 7:
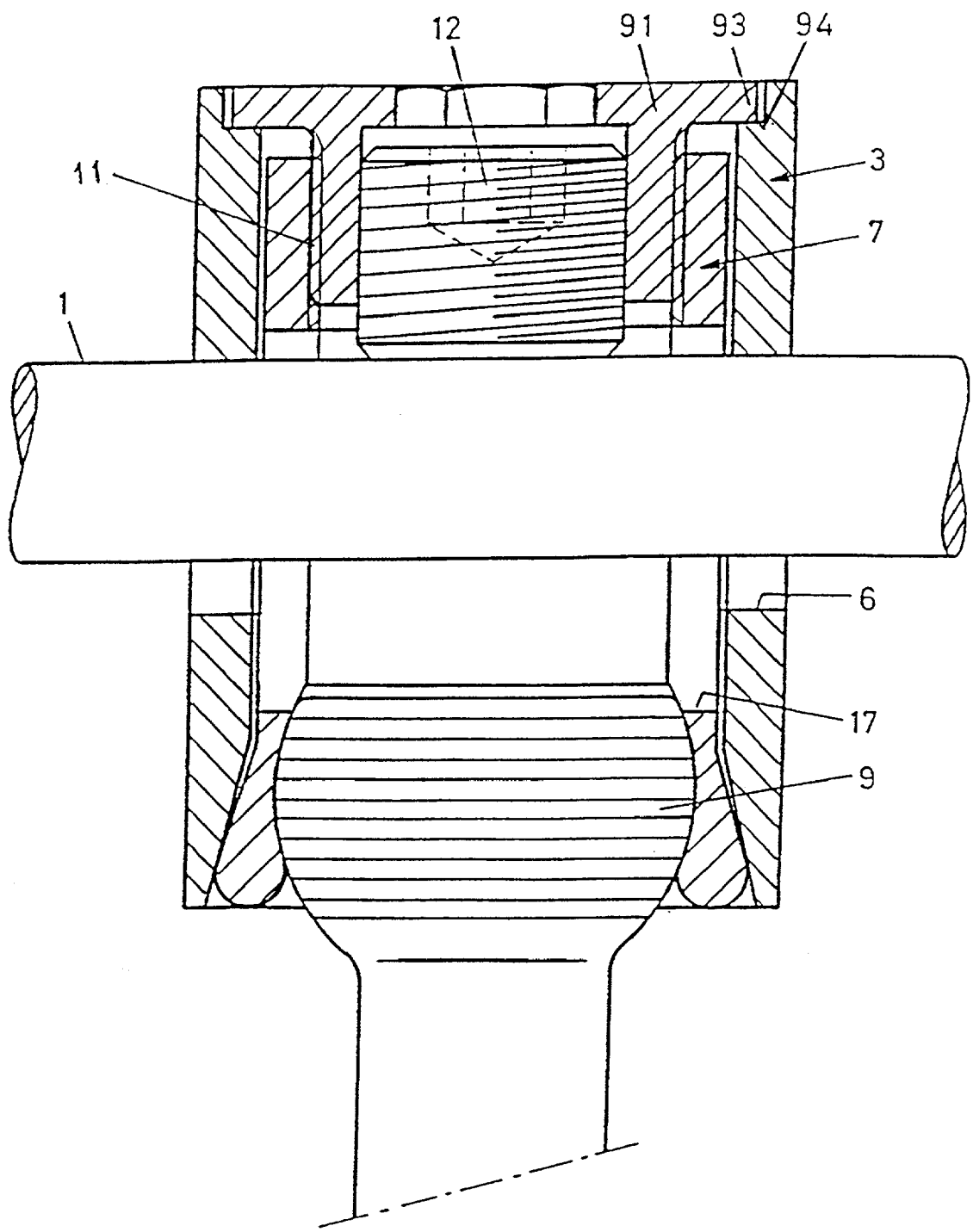
FIG. 7: a longitudinal section through one variant of the device illustrated in FIG. 6 with a set screw integrated into a locking screw.

The variant illustrated in FIG. 7 of the device according to this invention differs from the device illustrated in FIGS. 1 through 3 only in the design of the locking screw 91 and the positioning of the through hole 6 with respect to the through hole 17. The collet chuck 7 is provided with an inside thread 11. A locking screw 91 which is screwed into the inside thread 11 and a set screw 12 which is integrated into the locking screw 91 serve to lock the spherical head 9 and the longitudinal bar 1. The body 3, which is designed in one piece by analogy with FIGS. 1 through 3, is provided with a turning 94 at the top, accommodating the shoulder 93 of the locking screw 91. The through hole 6 is positioned in body 3 with respect to the through hole 17 in the collet chuck 7 in such a way that only spherical head 9 is locked when locking screw 91 is tightened. The longitudinal bar 1 is secured afterwards by means of the set screw 12. As long as this set screw 12 is screwed completely into the locking screw 91, and the locking screw 91 has been screwed back to the extent that the longitudinal bar 1 touches the lower edge of the through hole 6 in the body 3, the spherical head 9 can be secured or removed. Furthermore, the collet chuck 7 is released again from the tightened state when the locking screw 91 is screwed back. To accommodate the longitudinal bar 1, the collet chuck 7 may be provided with a through hole 17 according to FIG. 4, with a channel 54 which is open at the top according to FIG. 9, or with a channel 42 according to FIG. 8 which is open at the side. In these two cases, either a two-piece design of body 3 or a design according to FIGS. 11 and 12 is advantageous to facilitate insertion of the longitudinal bar. However, with the two-piece design, the two parts of the body 3 must be designed so that the top part 53 presses directly on the bottom part 52 and not on the longitudinal bar 1 even after bracing.

The variant shown in FIG. 8 of the device according to this invention differs from the variant illustrated in FIG. 4 only in that, in contrast with the collet chuck 71, the collet chuck 74 has a channel 42 that is open at the side instead of having a through hole 17 to accommodate the longitudinal bar 1, but the slot 22 does not extend into this open channel.

The variant shown in FIG. 9 of the device according to this invention differs from the variant illustrated in FIG. 4 only in that, in contrast with the collet chuck 71, the collet chuck 72 has a channel 54 that is open at the top instead of a through hole 17 to accommodate the longitudinal bar 1, and the slot 22 does not extend into this open channel. To prevent the collet chuck 72 from collapsing when the adjusting nut 26 is tightened, the thread must be designed so that negligible radial forces occur in tightening. A sawtooth thread, for example, would meet this requirement.

The variant shown in FIG. 10 of the device according to this invention illustrates the use of a collet chuck 75, which is provided with an inside thread 11 instead of an outside thread 27, in contrast with the collet chuck 72 illustrated in FIGS. 5 and 9. A set screw 56 with an outside thread 57 and a flange 58 serves as the clamping means. When tightened, the set screw 56 presses against the longitudinal bar 1, which presses in turn on the bottom part 52 of the body 3. This bracing of the bottom part 52 and the collet chuck 75 locks the spherical head 9 of the pedicle screw 2, as illustrated in FIG. 2. The top part 53 of the body 3 prevents widening of the collet chuck 75 when the set screw 56 is tightened. The top part 53 rests on the shoulder 63.

The variant shown in FIG. 11 of the device according to this invention differs from the variant illustrated in FIG. 6 only in that the collet chuck 76, in contrast with the collet chuck 73, has a channel 42 that is open at the side instead of a through hole 17, and the slots 22 do not extend into the channel.

According to FIG. 13, the through hole 6 in the body 3 is preferably open at the side (80) to permit unhindered insertion of longitudinal bar 1.

The variant shown in FIG. 12 of the device according to this invention differs from the variant illustrated in FIG. 11 only in that, in contrast with the collet chuck 76, the collet chuck 77 has a channel 54 that is open at the top to accommodate the longitudinal bar 1. According to FIG. 14, the through hole 6 in the body 3 is open toward the top (81) for unhindered insertion of the longitudinal bar 1.

The variant shown in FIG. 13 of the device according to this invention differs from the variant illustrated in FIG. 11 only in that a through hole 80 which is open at the side is provided in the body 3.

The variant shown in FIG. 14 of the device according to this invention differs from the variant illustrated in FIG. 12 only in that a through hole 81 which is open at the top is provided in the body 3.

What is claimed is:

1. A spinal fixation system comprising:
   a longitudinal member positionable along a spinal column;
   a fastener having a head, the fastener being configured and dimensioned for engaging vertebrae; and
   a connector for coupling the fastener and longitudinal member comprising:
   a body having a through hole extending from a top surface to a bottom surface, and a first opening in a side surface for receiving the longitudinal member;
   a collet chuck with at least a portion slideably received in the through hole of the body, the collet chuck having internal threads and having a second opening for receiving the longitudinal member, the second opening being alignable with the first opening, and a plurality of resilient tongues defining a chamber for receiving the fastener head therein; and
   a locking element threadably associated with the internal threads of the collet chuck for releasably locking movement of the longitudinal member with respect to the collet chuck;
   wherein engagement of the body with the tongues of the collet chuck permits inward movement of the tongues to secure the fastener at a surgeon selected angle.

2. The spinal fixation system of claim 1 wherein the chamber has a substantially spherical shape.

3. The spinal fixation system of claim 2 wherein the fastener head has a substantially spherical shape.

4. The spinal fixation system of claim 1 wherein the tongues comprise grooves or ribs for securing the fastener head in the chamber.

5. The spinal fixation system of claim 1 wherein the fastener head comprises grooves or ribs for securing the fastener head in the chamber.

6. The spinal fixation system of claim 1 wherein the locking element comprises a set screw, and threading of the set screw with the internal threads of the collet chuck permits contact between the set screw and longitudinal member for releasably locking movement of the longitudinal member.

7. The spinal fixation system of claim 1 wherein the internal threads are provided in an upper portion of the collet chuck.

8. The spinal fixation system of claim 1 wherein the body and collet chuck are disposed about a central axis.

9. The spinal fixation system of claim 1 wherein the collet chuck has upper and lower ends and a third opening extending through the ends, with the internal threads being disposed in the third opening.

10. The spinal fixation system of claim 1 wherein the collet chuck has a third opening extending through an upper end thereof and communicating with the chamber, with the internal threads being disposed in the third opening.

11. A spinal fixation system comprising:
    a longitudinal member positionable along a spinal column;

a fastener having a head and a threaded end for engaging a vertebra; and a connector for connecting the fastener and the longitudinal member comprising:

a body having top, bottom, and side surfaces, a first opening in the side surface for receiving the longitudinal member, and a second opening extending from the top surface to the bottom surface;

a collet chuck configured and dimensioned to be slideably received in the second opening of the body and having upper and lower ends, a third opening in the upper end with internal threading, a fourth opening alignable with the first opening of the body for receiving the longitudinal member, a plurality of resilient tongues, and a chamber defined by the tongues configured and dimensioned to receive the fastener head; and a threaded locking element for releasably fixing movement of the longitudinal member with respect to the first and fourth openings, wherein flexing of the tongues permits the fastener head to be received and retained in the chamber, and threading of the locking element with the internal threading of the collet chuck causes translation of the collet chuck and body with respect to each other.

12. The spinal fixation system of claim 11, wherein at least one of the tongues and fastener head are provided with grooves or ribs.

13. A spinal fixation system comprising:

a spinal rod positionable along a spinal column;

a bone fastener having a head and a threaded end portion for engaging a vertebra; and a connector for coupling the bone fastener to the spinal rod, the connector including:

a first member having a first end, a second end, a through hole extending therebetween, and a first rod receiving channel;

a second member at least partially slidably received in the through hole of the first member, the second member includes a top end, a second rod receiving channel substantially aligned with the first rod receiving channel when the second member is partially disposed within the first member, and a resilient bottom end defining a chamber for receiving the head of the bone fastener; and securing means associated with the top end of the second member for releasably fixing the position of the spinal rod with respect to the second member and for moving the second member with respect to the first member without the securing means directly engaging the first member;

wherein movement of the second member with respect to the first member causes the inward movement of the bottom end of the second member so that the position of the bone fastener is fixed with respect to the second member.

14. The system of claim 13, wherein the first and second members are each in the form of a hollow cylinder, the first and second members being coaxially arranged so that the second member can slide within the first member.

15. The system of claim 13, wherein the through hole of the first member defines a central axis and the first and second rod-receiving channels are substantially transverse to the central axis.

16. The system of claim 13, wherein the second member is pressed-fit within the through hole of the first member.

17. The system of claim 13, wherein the first and second members are rotationally locked with respect to one another.

18. The system of claim 13, wherein the bottom end of the second member includes at least one slot rendering the bottom end resilient so that the head of the bone fastener can be snap-fitted into the chamber.

19. The system of claim 13, wherein the securing means includes an externally threaded set screw.

20. The system of claim 13, wherein the chamber has a substantially spherical shape sized and configured to mate with the head of the bone fastener which has a corresponding substantially spherical shape.

21. The system of claim 20, wherein the chamber and the head have a roughened surface for securing the head in the chamber.

* * * * *